US012036016B2

(12) United States Patent
Bono

(10) Patent No.: US 12,036,016 B2
(45) Date of Patent: Jul. 16, 2024

(54) SYSTEM FOR CAPTURING PERSON-RELATED ACCIDENT DATA IN A VEHICLE

(71) Applicants: Caroline Bono, Hombrechtikon (CH); Rudolf Rothenbühler, Hombrechtikon (CH)

(72) Inventor: Caroline Bono, Hombrechtikon (CH)

(*) Notice: Subject to any disclaimer, the term of this patent is extended or adjusted under 35 U.S.C. 154(b) by 840 days.

(21) Appl. No.: 17/051,054

(22) PCT Filed: Apr. 24, 2019

(86) PCT No.: PCT/CH2019/000013
§ 371 (c)(1),
(2) Date: Oct. 27, 2020

(87) PCT Pub. No.: WO2019/204949
PCT Pub. Date: Oct. 31, 2019

(65) Prior Publication Data
US 2021/0236024 A1    Aug. 5, 2021

(30) Foreign Application Priority Data
Apr. 27, 2018  (EP) .................................. 18169880

(51) Int. Cl.
*A61B 5/11*    (2006.01)
*A61B 5/00*    (2006.01)
(Continued)

(52) U.S. Cl.
CPC .......... *A61B 5/1114* (2013.01); *A61B 5/0077* (2013.01); *B60Q 3/76* (2017.02);
(Continued)

(58) Field of Classification Search
CPC ....... A61B 5/0077; A61B 5/1114; B60Q 3/76; B60Q 3/80; G06T 7/20;
(Continued)

(56) References Cited

U.S. PATENT DOCUMENTS 7,044,742 B2 * 5/2006 Sumiya ................. G08B 23/00
434/350
7,495,547 B2 * 2/2009 Lich ..................... G08B 25/016
340/436

(Continued)

FOREIGN PATENT DOCUMENTS

DE    10 2015 208 358 A1    11/2015
JP    2009-69885 A    4/2009

OTHER PUBLICATIONS

International Search Report issued on Jul. 18, 2019 in PCT/CH2019/000013 filed on Apr. 24, 2019, 3 pages.

*Primary Examiner* — Eric J Messersmith
(74) *Attorney, Agent, or Firm* — Oblon, McClelland, Maier & Neustadt, L.L.P.

(57) ABSTRACT

A system for capturing person-related accident data in a vehicle, comprising at least one camera for capturing image data of at least one vehicle occupant, the camera being designed as a high-speed camera, a circular memory for storing the captured image data, and a control unit, which is designed to receive an accident commencement signal. The control unit controls the circular memory and/or the camera in such a way that the storing of the image data is ended at the end time, the end time lying after the receipt of the accident commencement signal by a predefined time interval. The person-related accident data comprise at least the image data stored in the circular memory.

12 Claims, 5 Drawing Sheets

Figure 1B:
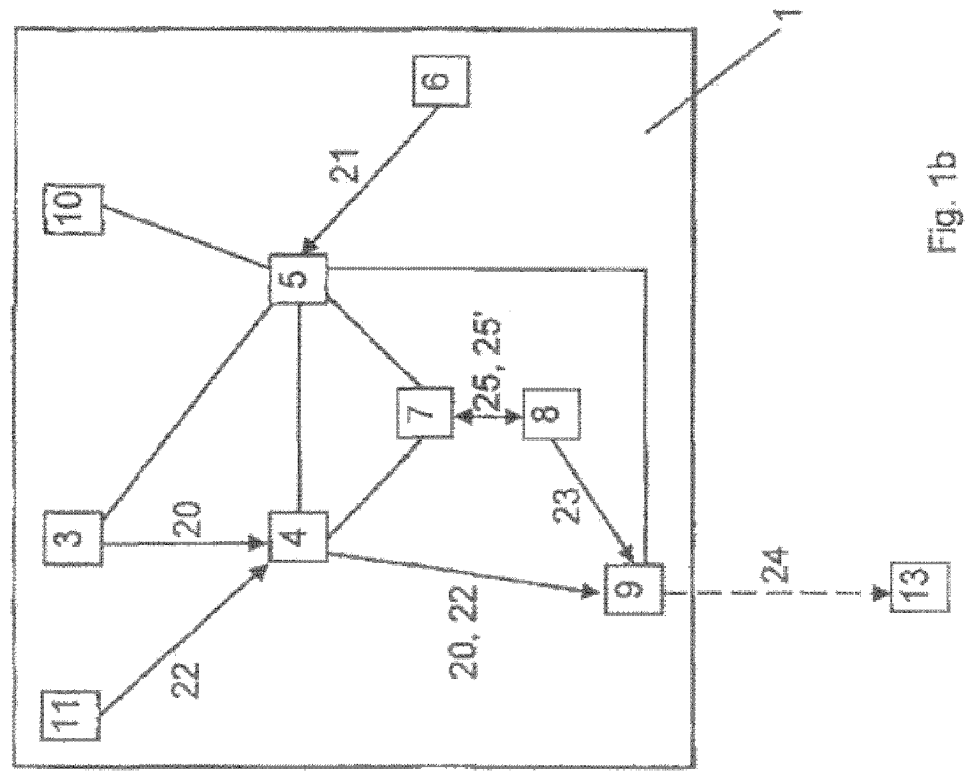

(51) Int. Cl.
| | |
|---|---|
| *B60Q 3/76* | (2017.01) |
| *B60Q 3/80* | (2017.01) |
| *G06T 7/20* | (2017.01) |
| *G06V 20/59* | (2022.01) |
| *G06V 40/16* | (2022.01) |
| *G07C 5/00* | (2006.01) |
| *G07C 5/08* | (2006.01) |
| *G16H 10/60* | (2018.01) |
| *H04N 5/765* | (2006.01) |
| *H04N 23/56* | (2023.01) |
| *H04N 23/90* | (2023.01) |

(52) U.S. Cl.
CPC ............. *B60Q 3/80* (2017.02); *G06T 7/20* (2013.01); *G06V 20/59* (2022.01); *G06V 40/172* (2022.01); *G07C 5/008* (2013.01); *G07C 5/0866* (2013.01); *G16H 10/60* (2018.01); *H04N 5/765* (2013.01); *H04N 23/56* (2023.01); *G06T 2207/10048* (2013.01); *G06T 2207/30196* (2013.01); *G06T 2207/30268* (2013.01); *H04N 23/90* (2023.01)

(58) Field of Classification Search
CPC . G06T 2207/10048; G06T 2207/30196; G06T 2207/30268; G07C 5/008; G07C 5/0866; G16H 10/60; H04N 5/765; H04N 23/56; H04N 23/90; G06V 20/59; G06V 40/172; B60R 21/01552; B60R 11/04; B60R 25/102; B60R 2021/0027
See application file for complete search history.

(56) References Cited

U.S. PATENT DOCUMENTS

| | | | | |
|---|---|---|---|---|
| 8,335,616 | B2* | 12/2012 | Neal | B60R 25/00 |
| | | | | 701/45 |
| 9,191,992 | B2* | 11/2015 | Dimitri | H04M 1/72421 |
| 10,229,545 | B2* | 3/2019 | Chung | G08B 5/228 |
| 10,232,813 | B2* | 3/2019 | Loeffler | B60R 21/01 |
| 2008/0195261 | A1* | 8/2008 | Breed | G01S 15/10 |
| | | | | 701/2 |
| 2010/0060734 | A1 | 3/2010 | Chou | |
| 2010/0219944 | A1 | 9/2010 | McCormick et al. | |
| 2012/0105635 | A1 | 5/2012 | Erhardt et al. | |
| 2015/0251071 | A1* | 9/2015 | Steusloff | A63B 60/16 |
| | | | | 702/141 |
| 2017/0129435 | A1* | 5/2017 | Vitet | B60R 21/0136 |
| 2017/0274897 | A1 | 9/2017 | Rink et al. | |

* cited by examiner

SYSTEM FOR CAPTURING PERSON-RELATED ACCIDENT DATA IN A VEHICLE

The present invention relates to a system for capturing person-related accident data in a vehicle, a process for capturing person-related data in a vehicle and a process for establishing a medical diagnosis of at least one vehicle occupant after an accident.

DE 102014200567 A1 describes a process for transferring image and audio data from an accident of a vehicle to a further-processing location, for example, in the context of an automatically-generated emergency call (eCall). The data transferred may then, for example, be evaluated to assess the severity of material damage and personal injury.

US 2008/0195261 also describes a vehicle internal system with which it is possible to send an emergency call automatically to a rescue control centre in the event of an accident.

Due to a traffic accident a vehicle driver or other vehicle occupants may sustain various injuries. Particularly susceptible to injury during an accident, particularly a rear-end accident, are the cervical spine (due to a sudden and unforeseen movement of the head towards the fixed torso), the head itself and even the thorax, but also the torso and extremities. The various hurtling movements of the head towards the torso during the accident when held by the seatbelt, for example, occur within a very short space of time in the region of few hundred milliseconds. The consequential injuries and/or medical symptoms are designated as whiplash trauma (also cervical spine distortion or whiplash syndrome) and may extend in their severity from overstretched ligaments to spine fractures or fatal injuries.

However, unfavourable collision angles may also result in the holding function of the seatbelt failing with the consequence of unlimited multiple trauma, which can be proven by imagery.

However, most of the injuries occurring cannot be represented or are only difficult to represent in traditional image-providing medical procedures, for example, in X-ray diagnostics, which may, among other things, make a medical diagnosis and the provision of proof for payment claims on insurance policies due to long-term damage difficult.

The task of the present invention consists of providing an alternative or even improved system for capturing person-related accident data in a vehicle or even a process for capturing person-related accident data in a vehicle, particularly person-resalted accident data that can be considered when making a medical diagnosis and which allows a reconstruction and mapping of the entire sequence of the accident in a way that is true to reality.

This task is solved by a system for capturing person-related accident data, a vehicle, a process for capturing person-related accident data and a process for making a medical diagnosis. In so doing, the processes may also be embodied by the characteristics of the system and/or the vehicle below, or even the characteristics of the system and the vehicle or even the processes may also be used respectively between each other as embodiment.

A system according to the invention for capturing person-related accident data in a vehicle comprises at least one camera for capturing image data of at least one vehicle occupant, wherein the camera is designed as a high-speed camera, a circular memory for storing the captured image data and a control unit. The control unit is designed to receive an accident commencement signal and control the circular memory and/or the camera in such a way that storing the image data is completed by an end time, wherein the end time is after a predefined time interval after receiving the accident commencement signal. The person-related accident data comprise at least the image data stored in the circular memory.

In the following, a high speed camera designates a camera that is suitable for capturing a high number of frames per second (fps), in other words, that exhibits a high capturing speed, and therefore capturing occurrences that are particularly brief and/or happen particularly quickly. For example, as a camera, a high speed camera with a capturing speed of at least 700 fps, preferable at least 1000 fps may be used.

A circular memory is a digital memory with specified size or even storage capacity, in which data, in the present case among other things the image data captured by the high-speed camera is continuously stored. If the maximum size of the circular memory is reached and the circular memory is full, then the relevant oldest stored element is overwritten, so that that data is stored in a loop. Therefore, the graphical representation of the memory is a ring shape.

The circular memory may, for example, be implemented by suitable software, by means of which the storing and reading of data in a digital memory is controlled accordingly.

Preferably, the size of the circular memory is sufficient to store frames captured by the high-speed camera for a time interval of several seconds, for example, 10 s or 20 s, before overwriting this again. The storage capacity needed therefore depends both on the desired duration of storing (in other words, the desired duration of an occurrence to be stored as image data in the circular memory) or even the desired capturing duration (in other words, the desired duration of a filmed and stored video sequence), as well as on the capturing speed of the high-speed camera and the size (in other words, quantity of data) of the image data to be stored.

With the system according to the invention for capturing person-related accident data, for example, it is possible to film a vehicle occupant in a vehicle continuously and to store the captured image data in the circular memory. Due to the large amount of data occurring, the image data not generally needed in the circular memory is overwritten by newly-captured image data after a predetermined time interval dependent on, among other things, the size of the circular memory. In the case of an accident, storing new image data is stopped after an established time to prevent accident-relevant data being overwritten again. Therefore, the circular memory comprises accident-relevant data after storing has finished, in other words, in particular capturing of the vehicle occupant immediately after the accident or even while the accident is happening.

Due to the high capturing speed of the camera, for example, it is possible for an evaluation of the image data to represent the accident-related acceleration and braking of the body of the vehicle occupant that occur essentially within a few hundred milliseconds in slow motion and therefore be able to draw conclusions as to possible injuries of the vehicle occupant, in other words, to analyse the accident event from a medical point of view (designated in the following as medical accident analysis). In so doing, the circular memory ensures, for example, that the quantity of data to be analysed is not too big and that data not needed are overwritten, in other words, are not stored or even that in the circular memory essentially only such image data are stored that are relevant for a medical and in any case also legal accident analysis.

Such a medical accident analysis using the person-related accident data may, for example, improve an initial response to those involved in the accident (in other words, the at least once vehicle occupant) at the scene of the accident and/or in a medical facility, for example, at least to reduce the medical consequential damage. The medical accident analysis may, for example, also be used to advise on a continuing medical treatment of those involved in the accident and/or to be able to justify claims against an insurance policy, also particularly in legal disputes.

Preferably, the predefined time interval is established depending on a capturing duration corresponding to the storage capacity of the circular memory, wherein, in particular, the predefined time interval corresponds to at least a half, preferably at least two thirds of the capturing duration of the circular memory. Therefore, for example, it is ensured that the image data continues to be captured and stored for a sufficient period after the point at which the accident commences, and therefore suitable image data are available for a later medical accident analysis. Furthermore, image data in the circular memory are also captured in such a way that they have been captured at a time immediately before the accident and therefore, for example, comprise information on the position of the vehicle occupant, for example, a rotation and/or inclination of their head, at the time the accident commences. This information may, for example, also be used for a later medical accident analysis.

Preferably, the system further comprises a sensor for providing and accident commencement signal, for example, a sensor for capturing a state of the airbag and/or an accelerometer and/or a speed sensor. Therefore, for example, it is possible to provide the accident commencement signal based on the sensors.

Alternatively or additionally, the system further comprises an analysis unit for analysing the captured image data and providing the accident commencement signal depending on the analysed image data. As a result, for example, it is possible to use high accelerations and/or speeds of the vehicle occupants as a detection pattern for an accident. In particular, as a result, even the image data relevant for a medical accident analysis may be used as trigger for interrupting the storing, which may reduce the risk of an erroneous interruption of the storing of image data, as the accident commencement signal may therefore be provided independently of the sensors.

Preferably, the person-related accident data further comprise medical data of the at least one vehicle occupant, wherein the medical data are preferably stored in a second memory of the system, and/or the person-related accident data further comprise operating data of the vehicle, wherein the operating data are preferably stored in the circular memory. The medical data may, for example, comprise information on the previous illnesses and/or diagnoses and/or medication, on medication incompatibilities and/or allergies and/or previous injuries and/or implants and/or medical procedures undergone etc. of the at least one vehicle occupant.

By providing medical data of the at least one vehicle occupant, for example, it is possible to consider these in an initial treatment of the vehicle occupant who has been in an accident and therefore improve the initial treatment. The operating data of the vehicle, also designated as physical values of the vehicle, during or even slightly before the accident event, for example, the speed or acceleration of the vehicle may, for example, also be used for a medical accident analysis.

Preferably, the camera for capturing the image data is suitable for multiple vehicle occupants and/or the system comprises several cameras designed as high-speed cameras.

In this way, it is possible, for example, to capture and store person-related accident data (particularly image data) of several, preferably all occupants of a vehicle. In addition it is possible, for example, to film at least one vehicle occupant with several high-speed cameras, preferably from various angles of view, for example, to be able to generate a three-dimensional representation of the movement of the vehicle occupant during the accident and therefore further improve the medical accident analysis.

Preferably, the system further comprises at least one illumination device for illuminating the at least one vehicle occupant, wherein the illumination device is preferably controlled by the control unit in such a way that it is switched on at least from receiving the accident commencement signal until the end time. Through the illumination device, for example, it is possible to capture and store images with good quality, particularly also in bad light such as, for example, at night, and therefore to achieve a good evaluability of the images. On the other hand, it is possible with the illumination, for example, to reduce the resolution of the high-speed camera with which the images are captured and therefore to reduce the quantity of data to be stored. The illumination may therefore be done in the infrared light range and the image capturing may also be done through an infrared camera by means of an infrared camera.

Preferably the system further comprises a preferably protected second memory, in other words, a hard disk memory and/or an SD card and/or a memory stick, for storing at least the image data stored in the circular memory and/or the system further comprises a transfer unit preferably for transferring the person-related data wirelessly and/or encrypted to an external location and/or an external memory and/or an externally-protected server, particularly as a cloud. Therefore, for example, it is possible to provide the person-related accident data for a medical accident analysis. By transferring the person-related accident data to an external location, this may, for example, be used by a first-aider and/or a first-treating doctor for an improved assessment of the medical condition of the at least one vehicle occupant. By storing in an internal memory of the system, the person-related accident data may, for example, be used for a later medical accident analysis, for example, by a first- or later-treating doctor and/or an expert or read on site by a first-aider. The encryption of the data is used for confidentiality and/or data protection and prevents unauthorised access to the data.

Preferably, the system further comprises an analysis unit for analysing the captured image data, wherein the analysis unit is designed in such a way as to compare a face of the at least one vehicle occupant with at least one stored face. In so doing, for example, it is possible to provide a rescue control centre even before the first-aider gets to the site of the accident, the identity of the at least one vehicle occupant and/or provide the correct medical data using the face and person detection system.

A vehicle according to the invention comprises a system described above for capturing person-related accident data. Therefore, it is possible, for example, to provide a vehicle with which the effects described above in relation to the system may also be achieved.

A process according to the invention for capturing person-related accident data in a vehicle comprises the steps: capturing image data of at least one vehicle occupant by means of at least one camera, wherein the camera is designed as a high-speed camera, storing the captured image data in a circular memory and receiving an accident commencement signal by means of a control unit, wherein the control unit controls the circular memory and/or the camera in such a way that storing the image data is finished at an end time, wherein the end time is at a predefined time interval after receiving the accident commencement signal and wherein the person-related accident data comprise at least the image data stored in the circular memory. Therefore, the effects described above in relation to the system, for example, may also be achieved with a process for capturing person-related accident data.

A process according to the invention for making a medical diagnosis of at least one vehicle occupant after an accident comprises the steps: providing person-related accident data that have been captured by a system and/or vehicle described above and/or in a process described above, and analysing the person-related accident data by a first-aider and/or a treating doctor and/or an expert and/or a further specialist person. Therefore it is possible, for example, to analyse the image data in case of an accident for immediate medical analysis make already in advance, in particular before an (initial) investigation of the person involved in the accident, an estimation of the physical condition and possible injuries of the person involved in the accident and/or use it to support making a medical diagnosis, particularly in connection with a medical investigation of the person involved in the accident and/or to review and/or even correct a medical diagnosis afterwards.

Preferably, for making the medical diagnosis, the image data comprising the person-related accident data are analysed in such a way that at least one movement process of a head of at least one vehicle occupant is captured during the accident, preferably as a relative movement, particularly in relation to an upper body and/or shoulder region of the at least one vehicle occupant. In particular, the entire body with head, neck, thorax, arms, torso and in any case partial parts of the lower extremities are captured. Therefore, it is possible, for example, to draw conclusions as to the injuries to the vehicle occupants due to the accident.

Further characteristics and purposes of the invention are produced by the description of illustrative examples using the appended drawings.

Figure 1A:
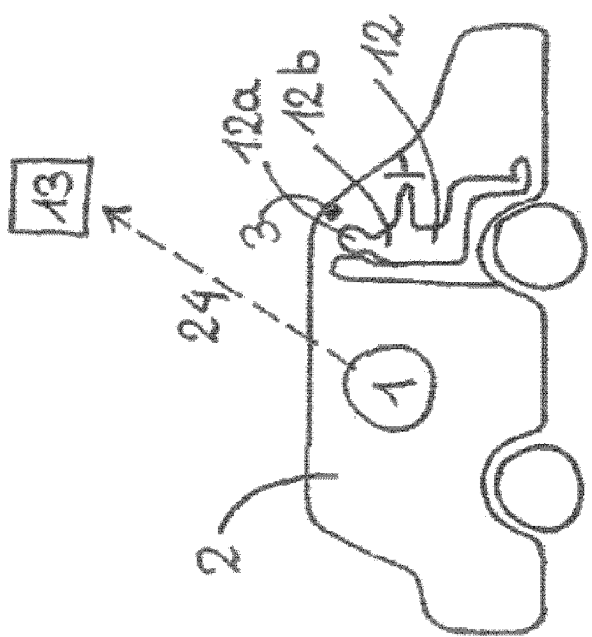
Figure 2:
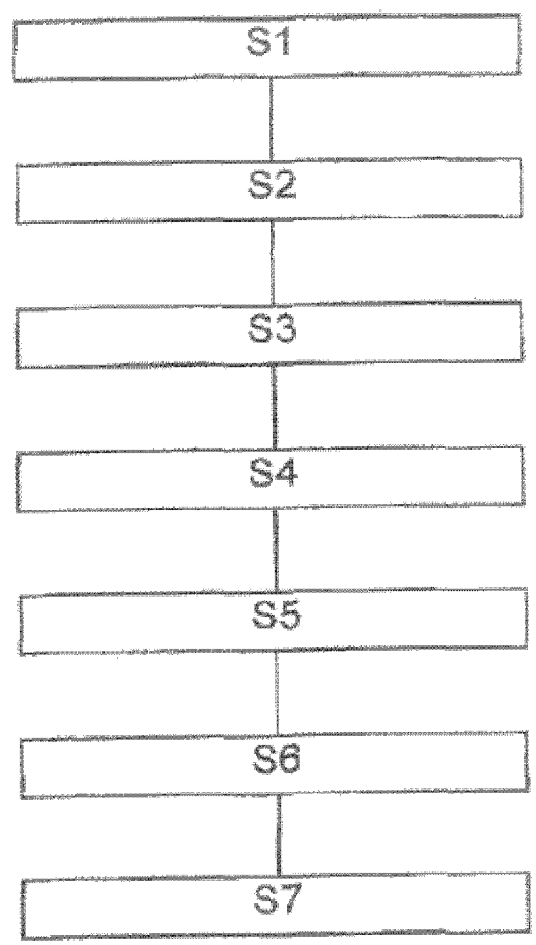
Figure 3:
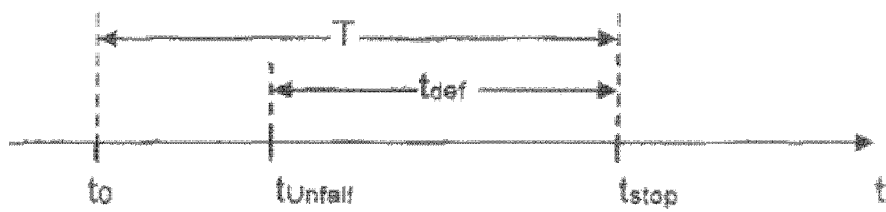
Figure 4:
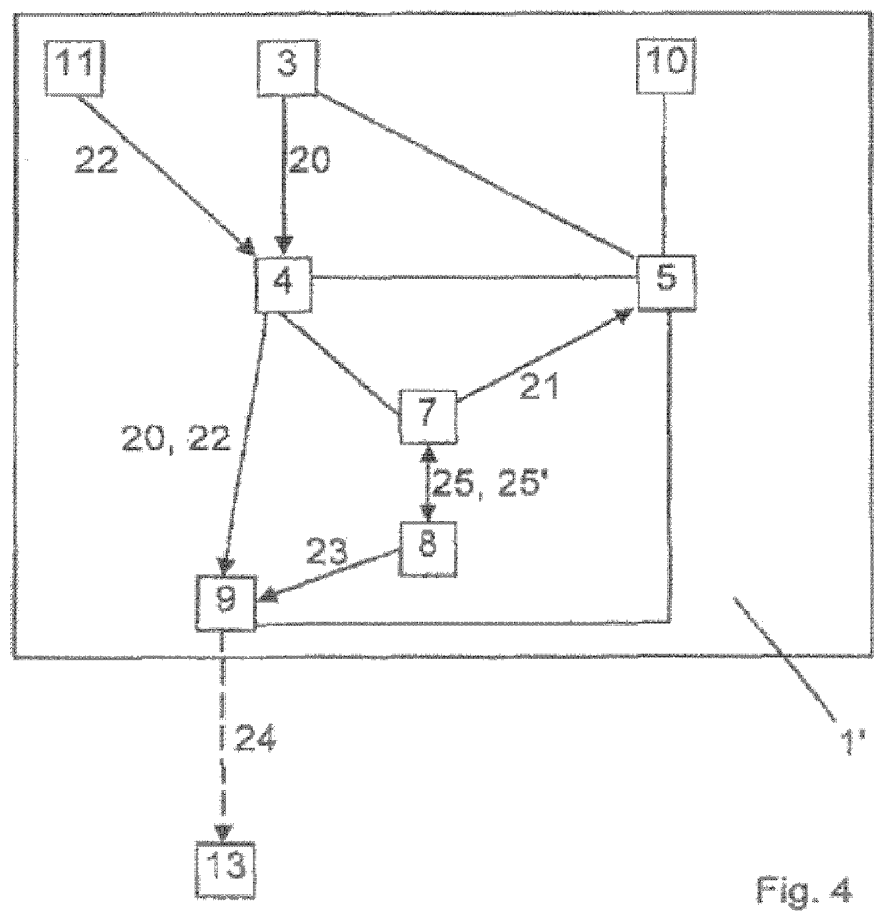
Figure 5:
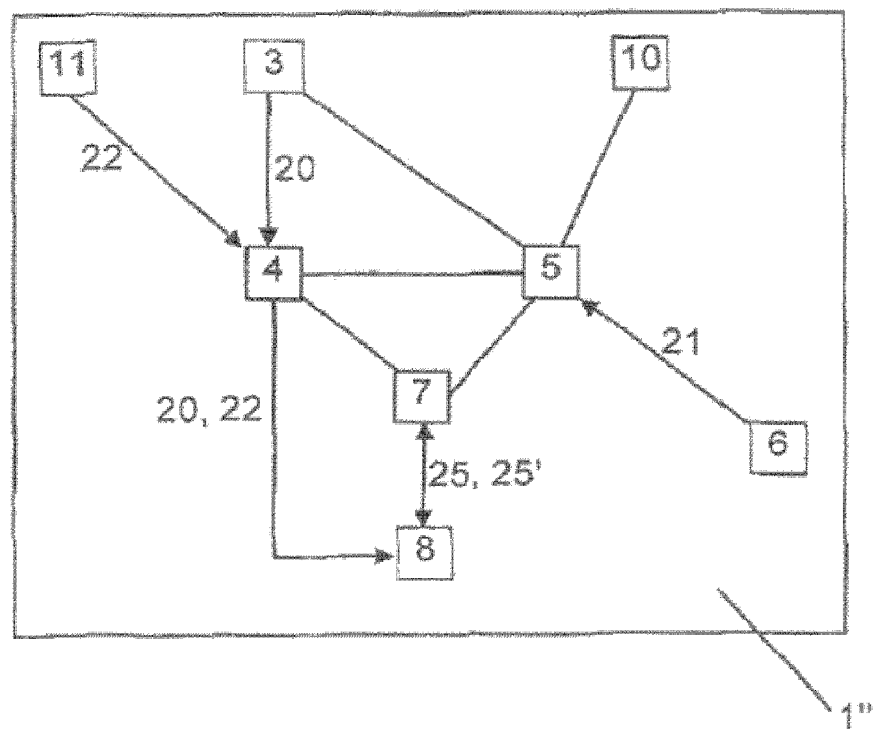

FIG. 1a is a schematic view of a vehicle with a system according to a first illustrative embodiment of the present invention which is shown schematically in FIG. 1b, FIG. 2 shows schematically a process for capturing and analysing person-related accident data by means of the system shown in FIG. 1a and FIG. 1b, FIG. 3 shows a time axis that schematically shows the storage duration of the circular memory in relation to an accident detection time, FIG. 4 is a schematic view of a system according to a second illustrative embodiment of the present invention and FIG. 5 is a schematic view of a system according to a third illustrative example of the present invention.

In the following, with reference to FIGS. 1a and 1b a first illustrative example of the present invention is described. FIG. 1a shows a vehicle 2 with a vehicle occupant 12 and a schematically-represented vehicle internal system 1 for capturing person-related accident data, wherein the system 1 is shown for a transparent illustration schematically shown in FIG. 1b. The vehicle 2 shown as an example in FIG. 1a is a motor car, but it may also, however, be designed as a utility vehicle.

The vehicle internal system 1 for capturing person-related accident data essentially comprises at least one camera that is designed as a high-speed camera 3, a circular memory 4, a control unit 5 and a transfer unit 9.

The high-speed camera 3 of the system 1 is designed and arranged in the vehicle 2 in such a way that it is suitable for capturing a region of the vehicle interior, in which the vehicle occupant 12 is located, in other words, for capturing a video sequence in the form of images of the vehicle occupant 12. To do this, the high-speed camera 3 does not have to capture the entire body of the vehicle occupant 12, rather it is sufficient to capture an upper section of their body, particularly the head 12a, the neck and the upper body and/or the shoulder region 12b. Optimally the camera also captures the more distal regions of the body.

The high-speed camera 3 exhibits a high capturing speed, for example, at least 700 fps, preferably at least 1000 fps. The images of the video sequence are captured by the high-speed camera 3 as digital image data 20.

The circular memory 4 of the system 1 is provided at any location of the vehicle 2 and connected by means of a data connection, for example, a data cable, to the high-speed camera 3 and thus suitable for storing the image data 20 captured by the high-speed camera 3 in digital form. Alternatively, the circular memory 4 may also be an internal memory of the high-speed camera 3.

The circular memory 4 exhibits a storage capacity corresponding to a capturing duration T, in other words, captured by the high-speed camera 3 and image data 20 stored in the circular memory 4 remain for the capturing duration T in the circular memory 4 before they are overwritten by newly-captured image data 20. The storage capacity of the circular memory 4 may, for example, be selected such that it corresponds to a capturing duration T of at least 10 s, preferably at least 15, further preferably at least 20 s. These values are understood only as example data, the capturing duration may also be less than 10 s.

The system 1 further comprises a sensor 6 provided at a suitable located in the vehicle 2, said sensor being suitable for establishing an accident of the vehicle 2 and generating a corresponding accident commencement signal 21. For example, the sensor 6 may be an airbag sensor that captures a state of an airbag (not shown) of the vehicle 2 and when the airbag is activated generates an accident commencement signal 21, and/or the sensor 6 may be a speed or acceleration and/or rotation sensor which when a pre-set speed change or even a pre-set acceleration or even a predefined rotation is exceeded generates an accident commencement signal 21. Under the term "acceleration" also negative accelerations, e.g. braking is to be understood.

The system 1 further optionally comprises an operating data capturing unit 11, provided at a suitable location of the vehicle 2, for capturing operating data 22 of the vehicle 2, wherein the operating data capturing unit 11 is connected to the circular memory 4 with a data connection, for example, a data cable to store the operating data 22 in the circular memory 4, preferably in connection with the image data 20. The operating data capturing unit may, for example, be designed as an accelerometer and/or position sensor, for example, as GPS, for capturing an instantaneous speed or even position of the vehicle 2 as operating data 22.

Optionally, system 1 further comprises an illumination device 10 of the vehicle 2 designed and arranged in the vehicle 2 in such a way that it is suitable for illuminating the vehicle interior, particularly a region of the vehicle interior in which the vehicle occupant 12 is located.

Furthermore, the system 1 optionally comprises a second vehicle internal data memory 8 in which face recognition data 25' of the at least one vehicle occupant 12 and medical data 23 of the at least one vehicle occupant 12 are stored. The medical data 23 of the vehicle occupant 12 may, for example, comprise information on medication incompatibilities and/or allergies and/or previous injuries and/or implants and/or medical procedures undergone. The second data memory 8 may, for example, be designed as a hard disk and/or an SD card and/or a memory stick.

An also optional vehicle internal analysis unit 7 of the system 1 is connected through respectively one data connection (for example, a data cable) to the circular memory 4 and the second data memory 8 and is suitable for calculating face recognition data 25 from the image data 20 stored in the circular memory 4 and comparing these with the face recognition data 25' stored in the second data memory 8. To do this, the analysis unit 7 may contain a CPU, the operation of which is controlled by a computer program (software) for face recognition.

The transfer unit 9 of the system 1 is also arranged at any location in the vehicle 2 and is connected through respectively one data connection (for example, data cable) to the circular memory 4 and the second data memory 8 of the system 1. It is suitable for transferring the image data 20 and optionally the operating data 22 and medical data 23 as person-related accident data 24 by means of a wireless transmission process to an external location 13, preferably encrypted. To do this, the transmission unit 9 exhibits a data interface not shown.

The external location 13 may, for example, be a rescue control centre and/or a first-aider and/or a particular first-treating doctor or even a particular first-treating medical facility, for example, an accident clinic. The external location 13 may also be a data memory outside the vehicle, for example, an external server or a cloud.

A vehicle-internal control unit 5 of the system 1 is to be designed in such a way as to control the individual vehicle-internal components of the system 1. To do this, it is connected to the relevant components through data connections (for example, data cable). The control unit 5 may contain a CPU, the operation of which is controlled by a computer program (software). In particular, the control unit 5 is suitable for receiving the accident commencement signal 21 from the sensor 6 and thereupon controlling the high-speed camera 3, the circular memory 4, the analysis unit 7 and the transmission unit 9 in such way that they execute a process described with reference to FIG. 2.

The system 1 may, for example, be completely or partially provided as an extension or retrofit kit for the vehicle 2 or already be integrated in the vehicle 2. In this way, components already present in the vehicle 2 may be used for the system 1, for example, the sensor 6 may be a sensor already present in the vehicle 2 and/or the control unit 5 may be a control unit already present in the vehicle 2 which is served by a suitable computer program (software) for controlling the components of the system 1.

FIG. 2 shows schematically a process for capturing person-related accident data in the vehicle 2 described with reference to FIGS. 1a and 1b. In step S1, the high-speed camera 3 continuously films the vehicle occupant 12 during the trip, in other words, capturing image data 20 of the vehicle occupant 12, and transfers these to the circular memory 4. Optionally, at the same time, operating data 22 of the vehicle 2 is captured by the operating data capturing unit 11 continuously or discreetly, preferably at equidistant times during the trip, and also transfers them to the circular memory 4.

The image data 20 and operating data 22 are stored in the circular memory 4 in step S2, wherein the data is preferably stored in such a way that the operating data 22 captured at one time is assigned to the image data 20 captured at the relevant time. This time assignment of the operating data 22 and image data 20 may, for example, be done by embedding the operating data 22 into the image data 20, for example, by storing the operating data 22 as metadata of the time-assigned image data 20 or graphically integrated in the image data 20, for example as wording. Due to the limited storage capacity of the circular memory 4, the image data 20 and relevant operating data 22 are respectively only stored during the limited capturing duration T in the circular memory 4 and are then overwritten by new data again.

As the circular memory 4 exhibits a limited storage capacity as described above, it may be advantageous to process the image data 20 before storing it in the circular memory 4 in such a way that they comprise a smaller data quantity. For example, the image sections corresponding to the image data 20 may be compressed and/or the colour images captured by the high-speed camera 3 may be stored as greyscale images. In this way, suitable image-processing software (not shown) may be provided preferably integrated into the high-speed camera 3.

In step S3 an accident of the vehicle 2 is captured by the sensor 6, for example, by activation of an airbag and/or a significant reduction of the speed of vehicle 2 and/or a significant braking (negative acceleration) of the vehicle 2 and/or a significant rotation or inclination of the vehicle 2. Thereupon, the sensor 6 sends an accident commencement signal 21 to the control unit 5.

The control unit 5 then stops in step S4 storing the image data 20 and the operating data 22 in the circular memory 4. The end time $t_{stop}$ at which storing the data is finished, is at a predefined time interval $t_{def}$ after receiving the accident commencement signal 21 from time $t_{Unfall}$ through the control unit 5, as FIG. 3 shows. The predefined time interval $t_{def}$ is therefore at most at great as the time duration T corresponding to the storage capacity of the circular memory 4, in other words, $t_{def} \leq T$, and preferably corresponds to at least half, further preferably at least two thirds of the capturing duration T corresponding to the storage capacity of the circular memory 4. This ensures that image data 20 and operating data 22 captured at the time of the accident and shortly afterwards (in other words, particularly during the accident event) in the circular memory 4 are not overwritten any more.

Therefore, after finishing continuously storing of image data and operating data 22 in the circular memory 4, corresponding to the capturing duration T corresponding to the storage capacity of the circular memory 5 between a time to, that is temporally before the time $t_{Unfall}$ of capturing the accident commencement signal 21 by the control unit 5, and the end time $t_{stop}$ after capturing the accident commencement signal are captured. As the time $t_{Unfall}$ of capturing the accident commencement signal 21 can be assumed to be the accident time, therefore, data are present from a period shortly before and shortly after the accident.

With a storage capacity of the circular memory 4 corresponding to a capturing time of T=10 s, the predefined time interval may be, for example, $t_{def}$=5 s, so that after finishing storing the data in the circular memory 4 image data 20 and operating data 22 are stored which were captured during a period 5 seconds before the accident to 5 seconds after the accident. With a capturing duration of T=10 s and a predefined time interval of, for example, $t_{def}$=7 s, after finishing storing data in the circular memory 4 there are image data 20 and operating data 22 which have been captured during a period of 3 seconds before the accident to 7 seconds after the accident.

The time specifications for the capturing duration T mentioned here and the predefined time interval t def are only to be understood as example values, the capturing duration T and the predefined time interval t def may also deviate from the values mentioned in the context of the invention.

Finishing data storing may, for example, happen in that the control unit 5 issues at end time $t_{stop}$ a command to switch off the high-speed camera 3 and the operating data capturing unit 11 to the same, so that no new image data 20 and operating data 22 are generated any more and/or by the control unit 5 interrupting the storing itself by suitable actuation of the circular memory 4.

Furthermore, in step S4 the illumination device 10 is actuated by the control unit 5 in such a way that the illumination device 10 at least from receiving the accident commencement signal at time $t_{Unfall}$ until end time $t_{stop}$ is switched on and illuminates at least a region of the interior of the vehicle 2, in which the section of the body of the vehicle occupant 12 captured by the high-speed camera 3 is located.

In the next step S5, the image data 20 present in the circular memory 4 after finishing storing data are analysed by the analysis unit 7, for example, by means of face recognition software. The face recognition data 25 thus captured are compared with the face recognition data 25' stored in the second memory 8 and with sufficient correspondence of the two datasets, in other words, if the face of the vehicle occupant 12 captured by the high-speed camera 3 corresponds with a sufficiently high probability with the face captured in the memory 8, the medical data 23 of the recognised person stored in the second memory 8 are transferred to the transfer unit 9. Furthermore, in step S5, the image data 20 and operating data 22 present after finishing storing data in the circular memory 4 are also transferred to the transfer unit 9.

Face recognition may also be undertaken independently of the commencement of an accident, for example, at the start of the trip of vehicle 2 and/or at regular intervals while capturing image data 20.

The image data 20 and operating data 22 present in the circular memory 4 are then transferred in step S6 together with the medical data 23 as person-related accident data 24 to the external location 13. The transmission of the person-related accident data 24 is thus done wirelessly, for example, by radio, particularly by mobile radio or Internet and may, for example, be done together with an electronically-made emergency call (what is known as an eCall). Preferably, the person-related accident data 24 are transferred in encrypted form, for example, by means of OpenPGP, wherein the person-related accident data 24 are encrypted by the transfer unit 9 by means of a public key generated by the external location 13 and only able to be decrypted again by the corresponding secret (private) key by the external location 13. The public key may already be present in the transfer unit 9 or the transfer unit 9 may request this from the external location 13 before encrypting and transferring the data.

Then, in step S7, the transferred and encrypted person-related accident data 24 are evaluated by an authorised and/or appropriately-trained person, for example, an employee of the rescue control centre and/or a first-aider and/or a first-treating doctor, in other words, a medical accident analysis performed, for example, to obtain an initial estimation of the health condition of the vehicle occupant 12.

In particular, the image data may be evaluated for making a medical diagnosis in such a way that a movement process ideally of the entire body, particularly the head 12a of the vehicle occupant 12 during the accident is captured. In particular, in this case, the relative movement of the head 12a in relation to the upper body and/or shoulder region 12b of the vehicle occupant is analysed to be able to draw conclusions on injuries related to the accident in the region of the cervical spine.

FIG. 4 shows a vehicle-internal system 1' according to a second illustrative example of the present invention. The system 1' shown in FIG. 4 differs essentially from system 1 shown in FIG. 1b in that the analysis unit 7 connected to the circular memory 4 through a data connection is designed in such a way, for example, by means of a suitable image processing program in case of an accident of the vehicle 2 to generate an accident commencement signal 21 using the image data 20 stored in the circular memory 4 and forward this to the control unit 5. To do this, the analysis unit 7 may contain a CPU, the operation of which is controlled by a computer program (software) for image recognition. The accident commencement signal 21 may, for example, be generated by a movement of the vehicle occupant 12 recognised by the analysis unit 7, in particular an acceleration and/or speed of the vehicle occupant 12 exceeding a predefined limit.

As the accident commencement signal 21 in the system 1' shown in FIG. 4 is able to be generated directly from the captured and stored image data 20, the sensor 6 shown for capturing the accident in FIG. 1b is not needed.

In the system 1' shown in FIG. 4, the process shown schematically in FIG. 2 is changed as follows: in step S2 the image recognition of the image data 20 stored in the circular memory 4 is continuously undertaken by the analysis unit 7 during the trip of the vehicle 2. The analysis unit 7 recognises an accident of the vehicle 2 using the analysed image data 20, so it transfers in step S3 an accident commencement signal 21 to the control unit 5. Steps S1 and S4 to S7 of the process described with reference to FIG. 2 do not differ in the system 1' shown in FIG. 4 from those of the system 1 shown in FIG. 1b.

FIG. 5 shows a vehicle internal system 1" according to a third illustrative example of the present invention. The system 1" shown in FIG. 5 differs essentially from system 1 shown in FIG. 1b and system 1' shown in FIG. 5 in that the person-related accident data 24 is not transferred by means of a transfer unit to an external location, but is stored in the vehicle internal second data memory 8 or a further (not shown) vehicle internal data memory. To protect the person-related accident data 24 or even the second memory 8 in the event of an accident of the vehicle 2, the second memory 8 is preferably designed as a protected memory (black box).

In the process described with reference to FIG. 2, in the system 1" shown in FIG. 5 in step S5 the image data 20 and optional operating data 22 are not transferred to the transfer unit but to the vehicle internal second data memory 8, that may already comprise the optional medical data 23 and stored in it. Therefore step S6 of transferring the data to an external location shown in FIG. 2 is dispensed with. To evaluate the person-related accident data 24 (step S7), this may be read or even downloaded, for example, from the second data memory 8.

The characteristics described above of the three illustrative examples may also be combined in any way with each other. Therefore, for example, the system 1 shown in FIG. 1b and/or the system 1' shown in FIG. 4 may only comprise the second memory 8 for vehicle internal storing of person-related accident data 24 instead of the transfer unit 9, as described with reference to FIG. 5. Also, the person-related accident data 24 may be transferred both to the internal second memory 8 and also to the external location 13. For example, in system 1 and/or system 1", which has been described with reference to FIG. 1b or even FIG. 5 an accident commencement signal 21 may also be provided by the image data 20 being analysed by the analysis unit 7 (instead of or in addition to provision of the accident commencement signal 21 by sensor 6) and/or with the system 1' described with reference to FIG. 4, an additional accident commencement signal may be provided by a sensor 6.

The operating data 22 and/or medical data 23 comprise optional data in the person-related accident data 24, for example to enable better medical accident analysis or even a better (initial) care of the person involved in an accident. The person-related accident data 24 may also only comprise the image data 20. In this case, the vehicle internal system 1, 1', 1" for capturing person-related accident data 24 in the vehicle 2 may also be provided without the operating data capturing unit 11 or even without the internal second data memory 8 (if the system comprises a transfer unit 9). Furthermore, the system 1, 1', 1" for capturing person-related accident data 24 may also be provided without the analysis unit 7 and/or without the illumination device 10. In particular, the captured image data 20 may also be analysed by the control unit 5 itself instead of by the analysis unit 7.

Furthermore, the components of the vehicle internal system 1, 1', 1" may also be components already provided in the vehicle 2 for another usage and/or the components of the system 1, 1', 1" may be used for other tasks and/or functions, in other words, the components may experience multiple usage. For example, the high-speed camera 3 may also be assigned to an assistance and/or safety system of the vehicle 2, for example, to detect a microsleep of the vehicle occupant 12, and/or the sensor 6 and/or the operating data capturing unit 11 may be components already provided in the vehicle 2.

To simplify the description of the illustrative example, these are only undertaken in relation to one vehicle occupant. The vehicle internal system may also be suitable for capturing person-related accident data of several vehicle occupants. To do this, preferably several high-speed cameras are provided for capturing image data of the vehicle occupant and/or several circular memories for storing at least the image data.

In addition, a vehicle occupant may also be filmed by more than one high-speed camera from various viewing angles, for example, to generate a three-dimensional view of the vehicle occupant.

The invention claimed is:

1. A system for capturing image data of a movement of at least one vehicle occupant during an accident and for storing the image data for a later medical analysis, the system comprising:
    at least one high-speed infrared camera for capturing the image data of the at least one vehicle occupant, the camera having a capturing speed of at least 700 frames per second,
    a circular memory for storing the image data, the circular memory having a storage capacity corresponding to a capturing duration of at least 10 seconds,
    a control unit that is configured to receive an accident commencement signal and control the circular memory and/or the camera in such a way that storing the image data is finished at an end time, the end time being at a pre-defined time interval after receiving the accident commencement signal,
    at least one illumination device transmitting light in the infrared range for illuminating the at least one vehicle occupant, the illumination device being controlled by the control unit in such a way that it is switched on at least from receiving the accident commencement signal until the end time, and
    an analysis unit for analyzing the image data, the analysis unit being configured in such a way that a face of the at least one vehicle occupant is compared with at least one stored face.

2. The system according to claim 1, wherein
    the pre-defined time interval is established depending on the capturing duration corresponding to the storage capacity of the circular memory, and
    the pre-defined time interval corresponds at least to half of the capturing duration of the circular memory corresponding to the storage capacity of the circular memory.

3. The system according to claim 1, further comprising a sensor for providing the accident commencement signal.

4. The system according to claim 1, wherein the analysis unit is further for providing the accident commencement signal depending on the analyzed image data.

5. The system according to claim 1, further comprising a second memory for storing medical data of the at least one vehicle occupant.

6. The system according to claim 1, wherein the circular memory is further for storing operating data of a vehicle.

7. The system according to claim 1, wherein
    the camera suitable for several vehicle occupants, and/or
    the camera includes several cameras configured as high-speed infrared cameras.

8. The system according to claim 1, further comprising:
    a second memory for storing at least the image data stored in the circular memory; and/or
    a transfer unit for transfer of the image data to an external location and/or to an external memory.

9. A vehicle comprising the system for capturing the image data of the movement of the at least one vehicle occupant during the accident and for storing the image data for the later medical analysis according to claim 1.

10. A process for capturing image data of a movement of at least one vehicle occupant during an accident and for storing the image data for a later medical analysis, the process comprising:
    detecting the image data of the at least one vehicle occupant by means of at least one high-speed infrared camera,
    storing the detected image data in a circular memory,
    receiving an accident commencement signal by means of a control unit,
    controlling by the control unit the circular memory and/or the camera in such a way that storing the image data is finished at an end time, the end time being at a predefined time interval after receiving the accident commencement signal,
    transmitting light in the infrared range by means of an illumination device for illuminating the at least one vehicle occupant,
    controlling the illumination device by the control unit in such a way that it is switched on at least from receiving the accident commencement signal until the end time, and analyzing by means of an analysis unit the detected image data, the analysis unit being configured in such a way that a face of the at least one vehicle occupant is compared with at least one stored face.

11. The process according to claim 10, further comprising:
providing the image data to a first-aider and/or a treating doctor and/or an expert and/or a further specialist person,
wherein the first-aider and/or the treating doctor and/or the expert and/or the further specialist person analyzes the image data.

12. The process according to claim 11, wherein the image data is analyzed in such a way that at least one movement process of a head of the at least one vehicle occupant is detected during the accident.

* * * * *